United States Patent
Brooks (12) 
(10) Patent No.: US 6,482,853 B1
(45) Date of Patent: Nov. 19, 2002

(54) LACTATE THIOLESTER FOR CARDIAC ENERGY RESUSCITATION AND PREVENTION OF REPERFUSION INJURY AND USE AS AN ENERGY SUPPLEMENT DURING EXERCISE AND RECOVERY

(76) Inventor: George A. Brooks, 5101 Valley Life Sciences Bldg., Berkeley, CA (US) 94720-3140

( * ) Notice: Subject to any disclaimer, the term of this patent is extended or adjusted under 35 U.S.C. 154(b) by 0 days.

(21) Appl. No.: 09/615,555

(22) Filed: Jul. 12, 2000

(51) Int. Cl.⁷ .................. H01N 37/00; H01N 31/21; C07C 327/00; C07C 321/00
(52) U.S. Cl. .................. 514/513; 558/250; 560/147
(58) Field of Search .................. 560/147; 558/250; 514/513

(56) References Cited

U.S. PATENT DOCUMENTS 5,420,107 A * 5/1995 Brooks
5,667,962 A * 9/1997 Brunengraber et al.

OTHER PUBLICATIONS

WO 95/17900. Sharpe et al. (1994). Methods for the treatment of the central nervous system or eye involving pathogenic oxidation pathways.*
WO 95/34303. Sharpe et al. (1995). Method for the treatment, prevention or minimization of hair loss.*

* cited by examiner

*Primary Examiner*—Paul J. Killos
*Assistant Examiner*—Mahreen Chaudhry
(74) *Attorney, Agent, or Firm*—Pillsbury Winthrop LLP (57) ABSTRACT

The invention comprises a novel lactate compound for two unique purposes: (1) cardiac energy resuscitation and the treatment or prevention of reperfusion injury following ischemia, and (2) the provision of a fuel energy source to humans and other mammals during exercise and recovery. The novel lactate compound is particularly a lactate thiolester. Preferably, the thiol is selected from a cysteine or a methionine amino acid. In a particularly preferred form, the compound is a lactate N-acetyl ethyl ester of the cysteine or methionine amino acid. The most preferred compound is lactate N-acetyl cysteine thiolester (LNACE):

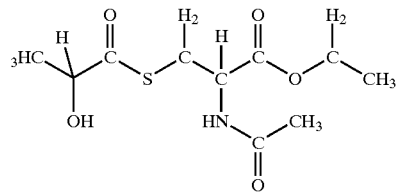

Depiction of lactate thiolester of N-acetyl cysteine (LNACE).

Further, the invention involves use of mixtures of lactate- and pyruvate compounds as well as hexoses (glucose and fructose), maltodextrins and electrolytes as adjutants to support LNACE in its specific purposes.

26 Claims, 5 Drawing Sheets

LACTATE THIOLESTER FOR CARDIAC ENERGY RESUSCITATION AND PREVENTION OF REPERFUSION INJURY AND USE AS AN ENERGY SUPPLEMENT DURING EXERCISE AND RECOVERY

U.S. PATENT DOCUMENTS CITED

| | | | |
|---|---|---|---|
| 4,970,143 | 11/1900 | Guidoux et al. | 435/1 |
| 5,075,210 | 12/1991 | Wikan-Coffelt | 435/1 |
| 5,283,260 | 2/1994 | Miller et al. | 514/563 |
| 5,294,641 | 3/1994 | Stanko | 514/490 |
| 5,420,107 | 5/1995 | Brooks | |
| 5,667,962 | 9/97 | Brunengraber et al. | |

OTHER PUBLICATIONS CITED

Allen, P. J., and G. A. Brooks. Partial purification and reconstitution of the sarcolemmal L-lactate carrier from rat skeletal muscle. *Biochem. J* 303:207–212, 1994.

Apstein, C. S., and L. H. Opie. Glucose-insulin-potassium (GIK) for acute myocardial infarction: a negative study with a positive value. Cardiovasc. Drugs Ther. 13: 185–189, 1999.

Bergman, B. C., E. E. Wolfel, G. E. Butterfield, G. D. Lopaschuk, G. A. Casazza, M. A. Homing, and G. A. Brooks. Active muscle and whole body lactate kinetics after endurance training in men. *J. Appl. Physiol.* 87: 1684–1696, 1999.

Brooks, G. A. Lactate: Glycolytic end product and oxidative substrate during sustained exercise in mammals—the "lactate shuttle." In, Comparative Physiology and Biochemistry—Current Topics and Trends, Volume A, Respiration—Metabolism—Circulation, R. Gilles (Ed.), Berlin, Springer-Verlag, 1984, pp. 208–218.

Brooks, G. A. Lactate production under fully aerobic conditions: The Lactate Shuttle during rest and exercise. *Federation Proc.* 45:2924–2929, 1986.

Brooks, G. A. Current concepts in lactate exchange. *Med. Sci. Sports Exerc.* 23:895–906, 1991.

Brooks, G. A. Mammalian Fuel Utilization During Sustained Exercise. *Comp. Biochem. Physiol.* 120: 89–107, 1998.

Brooks, G. A., M. A. Brown, C. E. Butz, J. P. Sicurello, and H. Dubouchaud. Cardiac and skeletal muscle mitochondria have a monocarboxylate transporter MCT1. *J. Appl. Physiol.* 87: 1713–1718, 1999.

Brooks, G. A., G. E. Butterfield, R. R. Wolfe, B. M. Groves, R. S. Mazzeo, J. R. Sutton, E. E. Wolfel and J. T. Reeves. Increased dependence on blood glucose after acclimatization to 4,300 m. *J. AppL. Physiol.* 70:919–927, 1991.

Brooks, G. A., G. E. Butterfield, R. R. Wolfe, B. M. Groves, R. S. Mazzeo, J. R. Sutton, E. E. Wolfel and J. T. Reeves. Decreased reliance on lactate during exercise after acclimatization to 4,300 m. *J. Appl. Physiol.* 71:333–341, 1991.

Brooks, G. A. and C. M. Donovan. Effect of training on glucose kinetics during exercise. *Am. J. Physiol.* 244 (Endocrinol. Metab. 7):E505–E512, 1983.

Brooks, G. A, H. Dubouchaud, M. Brown, J. P. Sicurello, and C. E. Butz. Role of mitochondrial lactic dehydrogenase and lactate oxidation in the 'intra-cellular lactate shuttle.' *Proc. Natl. Acad. Sci. USA* 96:1129–1134, 1999.

Brooks, G. A. and G. A. Gaesser. End points of lactate and glucose metabolism after exhausting exercise. *J. Appl. Physiol.* 49:1057–1069, 1980.

Brooks, G. A., T. D. Fahey, K. M. Baldwin, and T. P. White. EXERCISE PHYSIOLOGY: HUMAN BIOENERGETICS AND ITS APPLICATIONS, Third Edition, Mayfield, Mountain View, 2000.

Brooks, G. A., E. E. Wolfel, B. M. Groves, P. R. Bender, G. E. Butterfield, A. Cymerman, R. S. Mazzeo, J. R. Sutton, R. R. Wolfe, and J. T. Reeves. Muscle accounts for glucose disposal but not lactate release during exercise after acclimatization to 4,300 m. *J. Appl. Physiol.* 72:2435–2445, 1992.

Brouns, F. Aspects of dehydration and rehydration in sport. In, Nutrition and Fitness: Metabolic and Behavioral Aspects in Health and Disease, Simopoulos, A. P. and K. N. Pavlou (eds.), Karger Publ., Basel, 1997, pp. 63–80.

Brunet, J., M. J. Boily, S. Cordeau, and C. Des Rosiers. Effects of N-Acetylcysteine in the rat heart reperfused after low-flow ischemia: evidence for a direct scavenging of hydroxyl radicals and a nitric oxide dependent increase in coronary flow. *Free Radical Biology & Medicine* 19: 627–638, 1995.

Bunger, R. and R. T. Mallet. Mitochondrial pyruvate transport in working guinea pig heart. Work-related vs. carrier-mediated control of pyruvate oxidation. *Biochim. Biophys. Acta.* 1151:223–236, 1993.

Cremuzynski, L. et al. Low-dose glucose-insulin-potassium is ineffective in acute myocardial infarction: results of a randomized multicenter Pol-GIK trial. Cardiovasc. Drugs Ther. 13: 191200, 1999.

Connett, R. J., C. R. Honig, T. E. J. Gayeski and G. A. Brooks. Defining hypoxia: a systems view of $VO_2$, glycolysis, energetics and intracellular $PO_2$. *J. Appl. Physiol.* 68:833–842, 1990.

Davies, K. J. A., A. T. Quintanilha, G. A. Brooks and L. Packer. Free radicals and tissue damage produced by exercise. *Biochem. Biophys. Res. Comm.* 107:1198–1205, 1982.

Donovan, C. M. and G. A. Brooks. Endurance training affects lactate clearance, not lactate production. *Am. J Physiol.* 244 (Endocrinol. Metab. 7): E83–E92, 1983.

Dubouchaud, H., G. E. Butterfield, E. E. Wolfel, B. C. Bergman, and G. A. Brooks. Effect of endurance training on expression of lactate and other transport proteins in human skeletal muscle. *Am. J. Physiol. Endocrinol. Metab.:* 278: E571–E579, 2000.

Foster, D. W. From glycogen to ketones—and back. Diabetes 33:1188–1199, 1984.

Gaesser, G. A. and G. A. Brooks. Glycogen depletion following continuous and intermittent exercise to exhaustion. *J. Appl. Physiol.* 49:722–728, 1980.

Garcia, C. K., J. L. Goldstein, R. K. Pathak, R. G. Anderson, and M. S. Brown. Molecular characterization of a membrane transporter for lactate, pyruvate, and other monocarboxylates: implications for the Cori cycle. *Cell.* 76:865–73, 1994.

Gertz, E. W., J. A. Wisneski, W. C. Stanley, and R. A. Neese. Myocardial substrate utilization during exercise in humans: dual carbon-labeled carbohydrate isotope experiments. *J. Clin. Invest.* 82:2017–2025, 1988.

Gladden, L. B. Net lactate uptake during progressive steady-level contractions in canine skeletal muscle. *J. Appl. Physiol.* 71:514–520, 1991.

Gladden, L. B., R. E. Crawford, and M. J Webster. Effect of lactate concentration and metabolic rate on net lactate uptake by canine skeletal muscle. *Am. J. Physiol.* 266:R1095–101, 1994.

Halestrap, A. P. The mitochondrial pyruvate carrier. Kinetics and specificity for substrates and inhibitors. *Biochem. J.* 148:85–96, 1975.

Harrison, P. et al. Improvement by Acetylcysteine of Hemodynamics and Oxygen transport in Fulminant hepatic failure. *New England Journal of Medicine,* 324, no. 26, June 1991.

Jackson, V. N., N. T. Price, L. Carpenter and A. P. Halestrap. Cloning of the monocarboxylate transporter isoformn MCT2 from rat testis provides evidence that expression in tissues is species-specific and may involve post-transcriptional regulation. *Biochem. J.* 324( Pt 2):447–453, 1997.

Kirkwood, S. P., E. A. Munn, L. Packer and G. A. Brooks. Mitochondrial reticulum in limb skeletal muscle. *Am. J. Physiol.* 251: C395–C402, 1986.

Mazzeo, R. S., G. A. Brooks, D. A. Schoeller and T. F. Budinger. Disposal of [1-$^{13}$C]-lactate during rest and exercise. *J. Appl. Physiol.* 60:232–241, 1986.

Mentzer, J. et al. Effect of pyruvate on regional ventricular function in normal and stunned myocardium. *Ann. Surg.* 209: (5), May, 1990.

Molé, P. A., P. A. VanHandel and W. R. Sandel. Extra $O_2$ consumption attributable to NADH2 during maximum lactate oxidation in the heart. *Biochem. Biophys. Resh. Comm.* 85:1143–1149, 1978.

Newgard, C. B., L. J. Hirsch, D. W. Foster and J. D. McGarry. Studies on the mechanism by which exogenous glucose is converted into liver glycogen in the rat. A direct or indirect pathway. *J. Biol. Chem.* 258:1254–1256, 1983.

Pellerin, L., G. Pellegri, P. G. Bittar, Y. Chamay, C. Bouras, J. L. Martin, N. Stella, and P. J. Magistretti. Evidence supporting the existence of an activity-dependent astrocyte-neuron lactate shuttle. *Dev. Neurosci.* 20:291–299, 1998.

Price, N. T., V. N. Jackson, and A. P. Halestrap. Cloning and sequencing of four new mammalian monocarboxylate transporter (MCT) homologues confirms the existence of a transporter family with an ancient past. *Biochem. J.,* 329: 321–328, 1998.

Richter, E. A., B. Kiens, B. Saltin, N. J. Christensen and G. Savard. Skeletal muscle glucose uptake during dynamic exercise in humans: role of muscle mass. *Am. J. Physiol.* 254:E555–E561, 1988.

Rigobello, M. and A. Bindoli. Effect of pyruvate on rat heart thiol status during ischemia and hypoxia followed by reperfusion. *Molec. Cell. Biochem.* 22: 93–100, 1993.

Roth, D. A., and G. A. Brooks. Lactate transport is mediated by a membrane-borne carrier in rat skeletal muscle sarcolemmal vesicles. *Arch. Biochem. Biophys.* 279:377–385, 1990.

Roth, D. A., and G. A. Brooks. Lactate and pyruvate transport is dominated using a pH gradient-sensitive carrier in rat skeletal muscle sarcolemmal vesicles. *Arch. Biochem. Biophys.* 279:386–394, 1990.

Simpson, P. J., J. K. Mickelson, and B. R. Lucchesi. Free Radical Scavengers in myocardial Ischemia. *Fed. Proc.* 46: 2413–2421, 1987.

Stanley, W. C., E. W. Gertz, J. A. Wisneski, D. L. Morris, R. Neese and G. A. Brooks. Systemic lactate turnover during graded exercise in man. *Am. J. Physiol.* (Endocrinol. Metab. 12):249:E595–E602, 1985.

Stanley, W. C., E. W. Gertz, J. A. Wisneski, D. L. Morris, R. Neese and G. A. Brooks. Lactate metabolism in exercising human skeletal muscle: Evidence for lactate extraction during net lactate release. *J. AppL. Physiol.* 60:1116–1120, 1986.

Stanley, W. C., J. A. Wisneski, E. W. Gertz, R. A. Neese and G. A. Brooks. Glucose and lactate interrelations during moderate intensity exercise in man. *Metabolism* 37:850–858, 1988.

Sumegi, B., B. Podanyi, P. Forgo and K. E. Kover. Metabolism of [3-$^{13}$C]pyruvate and [3-$^{13}$C]propionate in normal and ischaemic rat heart in vivo: $^1$H- and $^{13}$C-NMR studies. *Biochem. J.* 312: 75–81, 1995.

Viguie, C. A., B. Frei, M. K. Shigenaga, B. N. Ames, L. Packer and G. A. Brooks. Antioxidant Status and Indices of Oxidative Stress During Consecutive Days of Exercise. *J. Appl. Physiol.* 75:566–572, 1993.

Wikman-Coffelt, A. et al. Alcohol and Pyruvate Cardioplegia. *J. Thorac Cardiovasc. Sug.* 101-509–16, 1991.

Wisneski, J. A., E. W. Gertz, R. A. Neese, and M. Mayr. Myocardial metabolism of free fatty acids. Studies with $^{14}$C-labeled substrates in humans. *J. Clin.Invest.* 79:359–366, 1987.

TECHNICAL FIELD

This invention relates generally to parenteral and enteral energy supplements, and, in particular, to a novel method and composition beneficial to functioning of heart and skeletal muscles of mammals with carbohydrate energy forms, antioxidants and electrolytes during ischemic and exercise stresses and subsequent recovery.

BACKGROUND OF THE INVENTION

This invention relates to a new lactate compound and a method of: (1) cardiac energy resuscitation and treating ischemia in mammalian hearts, lungs, veins, arteries and other organs or tissues, and (2) providing a supplemental energy source to active persons during exercise and recovery from exercise, and (3) providing energy to the heart and skeletal muscles during physical exercise and recovery from exercise. The invention is particularly directed to: (1) a method of cardiac energy resuscitation and treating an organ depleted of oxygen with a therapeutic amount of the novel lactate compound, (2) a method of replenishing energy in active individuals, (3) a method of maintaining blood sugar (glucose) in exercising individuals and restoring liver carbohydrate stores (glycogen) during recovery from exercise, and a method of hydrating and rehydrating individuals during exercise and recovery. The inventive method is constructed to benefit: (1) cardiac energy resuscitation following relief of cardiac ischemia as well as increase the viability of transplanted organs, and (2) increase the energy supply and vigor of active individuals.

DESCRIPTION OF THE ART

The invention takes advantage of discoveries of the classic (cell-cell, organ-organ) "Lactate Shuttle," and the "Intracellular Lactate Shuttle" mechanisms by Brooks (1984, 1998). The "Lactate Shuttle Hypothesis" holds that lactate plays a key role in the distribution of carbohydrate potential energy which occurs among various tissue and cellular compartments such as between: cytosol and mitochondria, muscle and blood, blood and muscle, active and inactive muscles, white and red muscles, blood and heart, arterial blood and liver, liver and other tissues such as exercising muscle, intestine and portal blood, portal blood and liver, zones of the liver, skin and blood, and astrocytes and neurons in the brain. Studies on resting and exercising humans indicate that most lactate (70–80%) is disposed of through oxidation, with much of the remainder converted to glucose and glycogen. Studies on canine muscles made to contract in situ also yield the result that lactate is rapidly oxidized (Gladden et al.). Lactate transport across cellular membranes occurs by means of facilitated exchange along pH and concentration gradients (Roth and Brooks 1990a, 1990b) involving a family of lactate transport proteins now called monocarboxylate transporters (MCT's) (Garcia et al., 1994; Price et al., 1998). Current evidence is that muscle and other cell membrane lactate transporters are abundant with characteristics of high Km and Vmax. There appears to be long-term plasticity in the number of cell membrane transporters, but short-term regulation by allosteric modulation or phosphorylation is not known to occur.

Key to recognition of an "Intracellular Lactate Shuttle" was recognition that in addition to cell membranes, mitochondria also contain monocarboxylate transporters (mMCT) and lactic dehydrogenase (mLDH). Mitochondrial MCT's exist in the mitochondrial inner membrane, and possibly also the outer membrane (FIG. 1), although presence of an outer mitochondrial membrane MCT is not essential because it is highly permeable. The Intracellular Lactate Shuttle also requires presence of mitochondrial lactate dehydrogenase (mLDH) located on the inner membrane and in the intra-membrane (periplasmic) mitochondrial space. mLDH is necessary to convert lactate, the predominant plasma and intracellular monocarboxylate, to pyruvate, for transport via mMCT into the mitochondrial matrix for catalysis by pyruvate dehydrogenase (PDH) and entry into the tricarboxylic acid (TCA) cycle. Therefore, mitochondrial monocarboxylate uptake and oxidation, rather than translocation of transporters to the cell surfaces, regulate lactate flux in vivo. Key discoveries in basic science are that lactate enters mitochondria, but that pyruvate is oxidized in the mitochondrial matrix. To take advantage of the Intracellular Lactate Shuttle, the invention described herein provides a means of delivering the energy fuel source, lactate, to working and stressed heart and muscle tissues. Key to the invention is providing a non-acidic lactate carrier molecule that has the advantage of being an effective antioxidant.

(1) Use of Lactate Thiolester for the Cardiac Energy Resuscitation and Prevention of Reperfusion Injury and in Organ Transplantation For hearts under stress of ischemia at least two considerations are important: (a) providing energy sufficient to optimize performance, and (b) preventing free radical damage blood supply is restored.

(a) Myocardial Substrate Utilization

Figure 1:
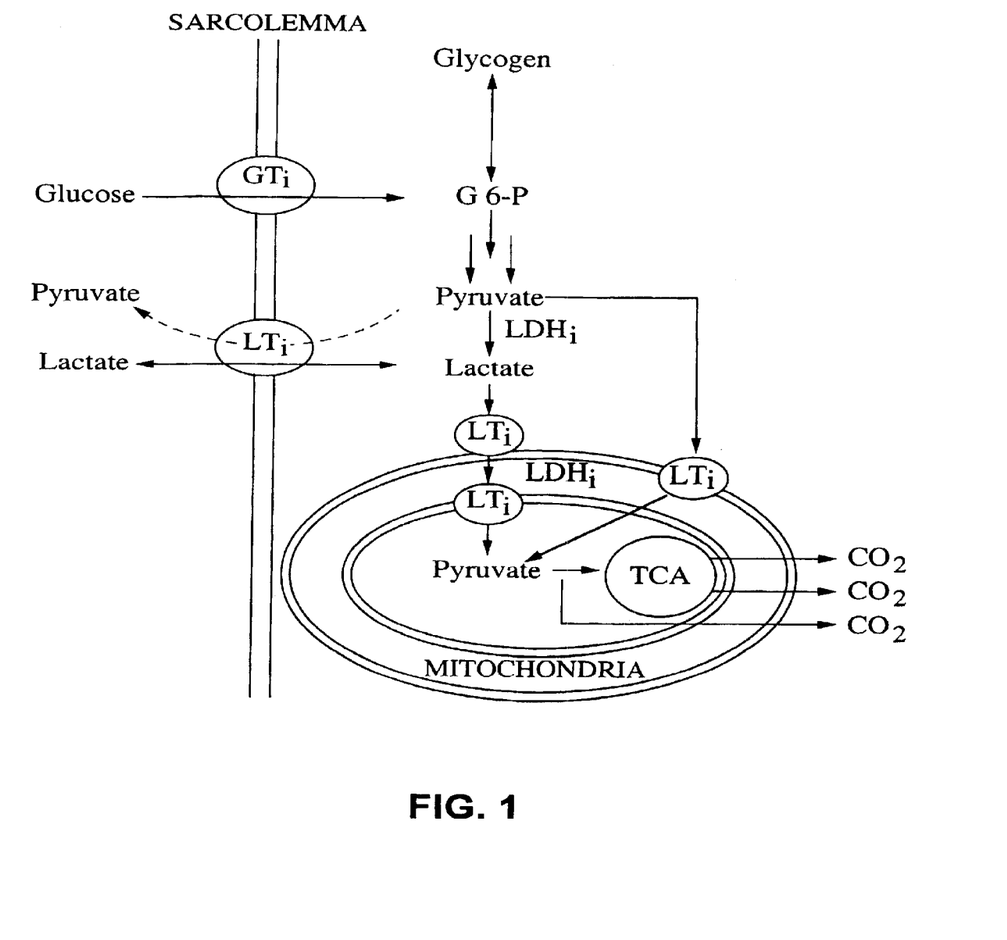
FIG. 1: Model of an "Intracellular Lactate Shuttle" showing the central role of lactate in coordinating lactate among and between cells. The model presupposes presence of a family of isoforms of lactate transport proteins ($LT_i$) which likely possess tissue specificity. Additionally, the model presupposes existence of mitochondrial LDH (mLDH), and lactate (monocarboxylate) transporter, or mMCT isoforms. From Brooks (1998, 1999).

Resting healthy hearts rely on exogenous, blood borne free fatty acids (FFA) as their main energy source with carbohydrate (CHO) derived fuel sources comprised of glucose and lactate playing secondary roles. For instance, in a resting person FFA may provide 80% of energy, glucose 5%, and lactate 15% (Gertz et al., 1988; Wisneski et al., 1987). However, under exercise and other stresses total energy demand increases and the fuel mix changes with the contribution of FFA falling to 40%, glucose use increasing absolutely but remaining at about 5%, and lactate the remainder (55%). During rest lactate is relegated to a minor role as an energy substrate for the heart because arterial [lactate] is low ($\leq 1.0$ mM). However, during physical exercise lactate predominates as the cardiac fuel energy source because production in working muscle and other tissues causes blood lactate concentration to rise to a level (2–20 mM) sufficient to be taken up and oxidized within the heart. As indicated in FIG. 1, exogenous lactate gains entry to cardiocytes because of cell membrane lactate transporters. Those transporters facilitate lactate flux down concentration and hydrogen ion ($H^+$) gradients. Within cardiocytes, lactate gains entry to mitochondria via another lactate transporter pool, also along concentration and $H^+$ gradients.

Realizing that CHO-derived energy sources increase cardiac performance, some investigators have attempted to promote cardiac energy resuscitation after ischemic attacks by providing glucose, sometimes with insulin and potassium. Currently used cardioplegic solutions containing glucose, insulin and potassium are sometimes referred to as GIK. Other investigators have attempted to provide pyruvate. However, from the physiological perspective such attempts are less than optimal, or misguided, because lactate, not glucose or pyruvate, is the major fuel for the heart under stress.

Recently, results of clinical trials (Ceremuzynski et al., 1999) have not confirmed viability of systemically administered GIK in the management of cardiac episodes. While GIK solutions do positively influence performance of stunned isolated hearts perfused and bathed in artificial solutions, unless GIK is administered into coronary arteries, significant effects on either cardiac performance or survival of ischemic episodes including MI is not to be expected (Apstein and Opie, 1999). Simply, GIK cannot be expected to have much effect because glucose never the major fuel for the heart. The obvious approach is to provide lactate in a form that can benefit cardiac metabolism.

(b) Ischemia-Reperfusion Injury

Ischemia is defined as the interruption of blood supply, hence the delivery of oxygen and nutrients to an organ and the subsequent removal of metabolic wastes. Examples of ischemic events include: (1) myocardial or cerebral infarction following obstruction of a branch of a coronary or cerebral artery, and (2) removal and storage of an organ prior to transplantation. In the case of myocardial infarction, prompt restoration of blood flow to the ischemic myocardium is a key component of the treatment. This is because mortality is directly related to infarct size which is related to the severity and duration of the ischemic event.

Despite the need to supply an organ cut-off from a normal blood supply with oxygen, it has been found that reperfusion injury may occur upon restoration of blood flow. This is because sudden return of oxygen to an oxygen-deprived tissue results from the production of reactive oxygen species (ROS), namely, hydrogen peroxide, hydroxyl radicals and superoxide radicals which are formed from both extracellular and intracellular sources (Davies et al.). ROS are highly reactive molecular species that, under normal conditions, are scavenged by endogenous defense mechanisms (Viguie et al.). However, under conditions of post-ischemic oxidative stress, ROS interaction with a variety of cellular components, causing peroxidation of lipids, denaturation of proteins, and interstitial matrix damage, resulting in increase of membrane permeability and release of tissue enzymes. In an attempt to minimize these undesirable side effects of perfusion, Simpson et al. suggest the use of an inhibitor of ROS production to protect the reperfused myocardium. Particularly, results of Simpson et al. suggest use of agents and inhibitors (e.g., allopurinol) that reduce ROS levels.

In a similar content, Brunet et al. suggest the use of acetylcysteine to reperfuse hearts. In particular, they conclude that N-acetylcysteine treatment decreases the production of ROS in reperfused rat hearts. Use of the amino acid, N-acetylcysteine is potentially efficacious in this regard as it is a precursor to the powerful cellular antioxidant glutathione (GSH).

In a further effort directed to protecting reperfused heart tissue, U.S. Pat. No. 5,075,210 herein incorporated by reference, discloses a process for reperfusing a heart for transplantation. The patent discloses a cardioplegic solution containing sodium chloride, potassium, chloride, calcium chloride, sodium bicarbonate, sodium EDTA, magnesium, chloride, sodium pyruvate and a protein.

U.S. Pat. No. 5,294,641, herein incorporated by reference, is directed to the use of pyruvate to prevent the adverse effects of ischemia. The pyruvate is administered prior to a surgical procedure to increase a patient's cardiac output and heart stroke volume. The pyruvate is administered as a calcium or sodium salt. The pyruvate can alternatively be an ester of pyruvate acid such as ethylamino pyruvate. Pyruvate is used because it is a cellular energy source, and potentially-though not practically (vide infra), may serve as an antioxidant.

With due consideration to growing acceptance of pyruvate as an effective component of reperfusion solution, it has been recognized that traditional pharmacological pyruvate compounds, such as salts of pyruvic acid, are not particularly physiologically suitable. For example, inorganic salts of pyruvate lead to the accumulation of large concentrations of inorganic ions (e.g., potassium, calcium or sodium) in body fluids. Accordingly, while potentially suitable to organ preservation, the salt-pyruvate compounds are not ideally suited to treating an organ or supplementing energy in an active person in vivo, and it is recognized that a need exists to deliver a monocarboxylate (pyruvate-like) compound which is more physiologically appropriate In this regard, U.S. Pat. No. 5,283,260, herein incorporated by reference, is directed to treatment of diabetes with a physiologically acceptable form of pyruvate. The patent discloses a pyruvate compound in the form of a covalently linked pyruvate-amino acid. By utilizing this type of pyruvate delivery system, the negative effects of inorganic-pyruvate salts are avoided. However, administration of large amounts of pyruvate-amino acid compounds may result in an amino acid nitrogen overload which could harm patients with liver and/or kidney pathology.

Similarly, U.S. Pat. No. 5,667,962, herein incorporated by reference, is directed to use of pyruvate thiolester for the prevention of reperfusion injury. The intention of that invention is to provide a compound comprising covalently linked pyruvate and N-acetylcysteine. However, design of the material is flawed in its purpose and mode of action.

Not withstanding use of compounds of complexes of pyruvate and antioxidant compounds in cardioplegia and organ transplantation procedures, as well as covalently linked compounds involving mixtures of pyruvate and amino acids with antioxidant characteristics such as embodied in the above identified US Patents, the emphasis on pyruvate as a monocarboxylate to deliver to stressed organs and tissues is misplaced. In fact, any attempts to utilize pyruvate as an agent to improve status of working heart and skeletal muscles results in a delayed response because lactate, not pyruvate, is the preferred compound exchanged ("shuttled") among organs, tissues, cells, and intracellular compartments. Tissue levels of lactate exceed those of pyruvate by 10 to 100-fold, and cell membrane monocarboxylate transporters are specific to lactate, not pyruvate. Beneficial effects of pyruvate administration accrue only after conversion to lactate, which is the preferred material for cell-cell exchange via the "Lactate Shuttle."

Figure 2:
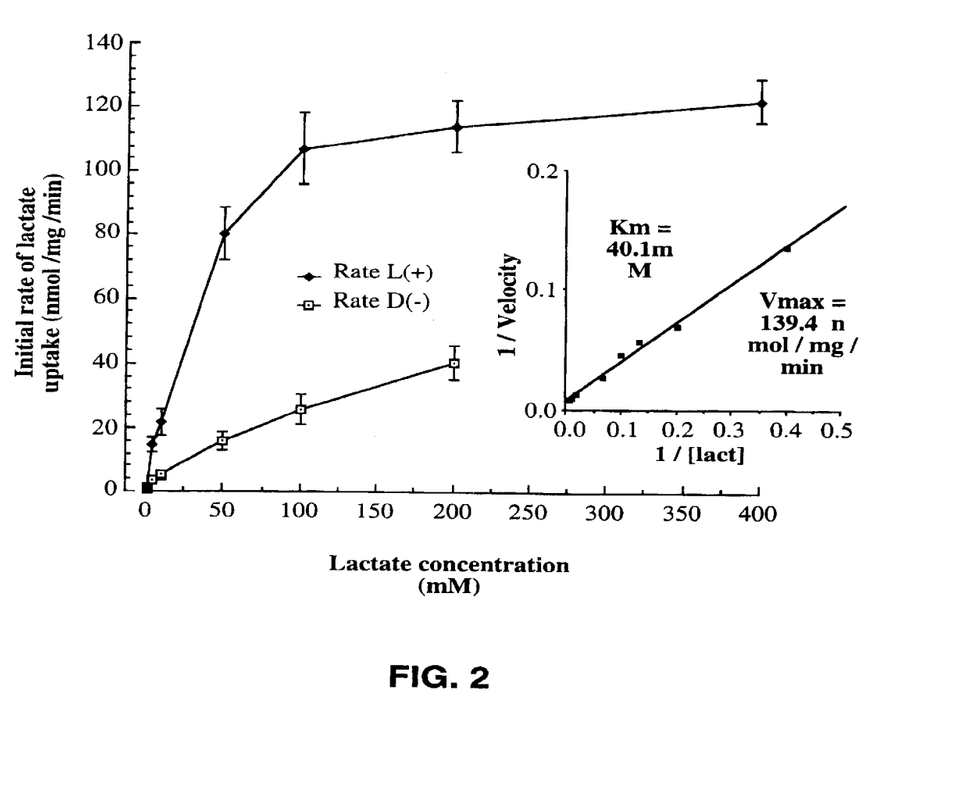

As stated by Sumegi et al. (p. 77) who utilized nuclear magnetic resonance spectroscopy (NMR) and [3-$^{13}$C] pyruvate tracer to study pyruvate metabolism in hearts of living rats: "The infused [3-$^{13}$C]pyruvate was quickly converted to [3-$^{13}$C]lactate in the blood of Wistar rats." [NB, this pyruvate→lactate conversion is due to presence of lactate dehydrogenase (LDH), an enzyme highly abundant in erythrocytes, such that in blood the lactate/pyruvate ratio is normally 10 and can increase an orderof magnitude under physiological stress (Brooks, 1998).] Surprised by their results and unable to explain them, with some trepidation Sumegi et al. went on to state (p. 80): "These data show that the extracellular lactate is preferentially taken up by a portion of cytoplasm which converts lactate to pyruvate and transfers it to the mitochondrial reticular network." However, in making the statement concerning conversion of lactate to pyruvate in cytoplasm, Sumegi et al. recognized a major problem in interpretation of their data. By failing to recognize existence of a mitochondrial form of lactic dehydrogenase (mLDH, FIG. 1), they had to: "assume that a fraction of the cytoplasm associated with the mitochondrial reticular network is specialized for converting the lactate to pyruvate, with the pyruvate being channeled to the mitochondria." [NB, in striated muscle (heart and skeletal) mitochondria do not exist as discrete organelles, but as part of a large, interconnected network, the Mitochondrial Reticulum (Kirkwood, et al.)]. As indicated by presence of mLDH (FIG. 2), the highly improbable assumption of Sumegi et al. is unnecessary, and the same physiological result is readily accomplished because of LDH.

Paradoxically, addition of exogenous lactate to the blood of mammals has alkalinizing effects because lactate removal from the blood, whether by oxidation or gluconeogenesis, requires a proton (in the ratio of 1: 1, protion:lactate anion) for transport and metabolism. Thus, by virtue of the acid/base chemistry in mammals, addition of lactate anion to plasma mitigates the presence of lactic acidosis.

A. In Proof of Cell Membrane Lactate Uptake, the Following Data from Roth and Brooks (1990a, 1990b) Are Presented Sarcolemmal vesicles were isolated from rat skeletal muscle and effects of various monocarboxylates including L(+) and D(−) lactate (FIG. 2), and other monocarboxylates were determined (Roth and Brooks, 1990a, 1990b). Results indicate saturation kinetics and stereospecificity for the L(+) compared to the D(−) isomer of lactate.

Figure 3:
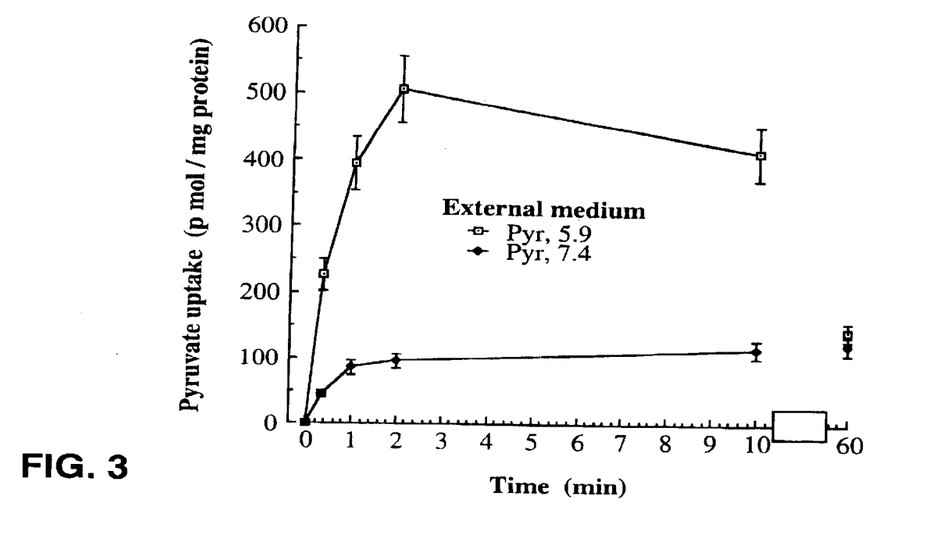
FIG. 3: L(+) pyruvate transport kinetics in rat sarcolemmal vesicles over time. Data are mean±SEM. Lineweaver-Burk plot of the L(+) lactate data. From Roth and Brooks, 1990b. Results show pH dependency for pyruvate transport, but values are far less than for lactate transport (FIG. 2).

These and other characteristics (e.g., pH dependency, temperature sensitivity and inhibition by known monocarboxylate inhibitors such as CINN, vide infra) indicate presence of a sarcolemmal lactate transport protein. Further, results indicate far greater affinity for lactate (FIG. 2), than for pyruvate (FIG. 3).

B. In Proof of Mitochondrial Lactate Uptake and Oxidation, the Following Data Are Presented (Brooks et al, 1999a).

Figure 4:
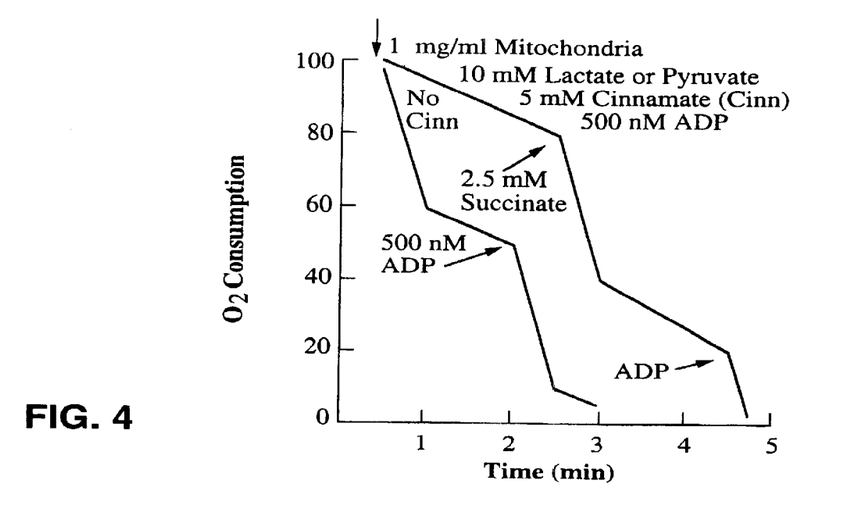

(1) Inhibition of mitochondrial Lactate and Pyruvate Uptake and Oxidation by CINN:

Traditionally, several substrates, and combinations of substrates have been used to study mitochondrial respiration in vitro. Pyruvate-malate has usually been used to probe mitochondrial Complex 1, succinate Complex 11, and TMPD+ascorbate Complex III. In contrast, lactate or lactate-malate has been infrequently used. However, pyruvate and lactate are known to share the sarcolemmal lactate transporter(s), and pyruvate gains access to the mitochondrial matrix by means of facilitated transport. Oxidation of lactate by isolated mitochondria is permitted by the presence of a mitochondrial pool of LDH which provides matrix pyruvate from exogenous lactate. To establish that lactate gains access to the mitochondrial matrix via facilitated exchange via a monocarboxylate (MCT) transport protein, we utilized polarography and inhibition by the known MCT inhibitor α-cyano -4-hydroxycinnamate (CINN). Results on rat liver mitochondria are shown in FIG. 4.

Results show CINN inhibition of pyruvate and lactate oxidation, but bypass of the CINN block by succinate, which gains access to the matrix by a different transport mechanism and which donates electrons to Complex II, in contrast to lactate and pyruvate which are NADH-linked substrates and donate electrons to Complex I. Additionally, results of experiments on rat liver mitochondria with 10 mM glutamate as substrate show no measurable effect of CINN on states 3 or 4 respiratory rate, RCR and ADP/O (data not shown). Absence of an effect of CINN on glutamate oxidation by isolated mitochondria is of value because, like pyruvate, glutamate is an NADH-linked substrate. Thus, the effect of CINN on pyruvate and lactate oxidation is upstream of Complex I.

Figure 5:
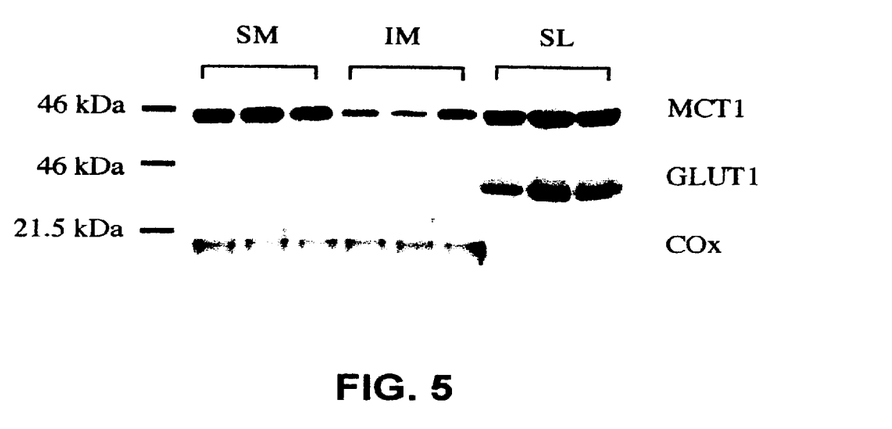
FIG. 5: Western blot showing responses of different rat cardiac muscle mitochondrial and cellular fractions probed with antibodies to MCT1, GLUT1 and cytochrome oxidase. The antibody to MCT1 responded strongly to subsarcolemmal (SM) and interfibrillar (IM) mitochondria and sarcolemmal (SL) membranes. Mitochondrial fractions reacted to cytochrome oxidase, but not to GLUT1; cell membranes did not react to cytochrome oxidase. From Brooks et al., 1999b.

(2): Presence of MCT1 or a MCT1 Homologue in Mitochondria: Mitochondria were isolated from skeletal muscle, rat liver and heart by standard techniques of cell fractionation. Subsequently, skeletal muscle mitochondria were probed with a polyclonal antibody to the C-terminus of rat MCT1 (N'-CPLQNSSGDPAEEESPV-C'), and results of a Western blot analysis displayed in FIG. 5. The results indicate presence of a mitochondrial protein which reacts with an antibody to the C-terminus of MCT1. To exclude the possibility of contamination from sarcolemmal MCT1 in the mitochondrial preparation, mitochondrial and cell membrane fractions were probed with antibodies to MCT1 and the cell membrane Glucose Transport Protein #1 (GLUT1). Scarcely detectable levels of GLUT1 in mitochondrial indicate minimal contamination from cell membranes in the mitochondrial preparation. Thus, it is evident that rat striated muscle mitochondria contain a monocarboxylate transporter with high homology to MCT1. Further, similar results have been obtained on human skeletal muscle and muscle mitochondria (Dubouchaud et al.).

Figure 6:
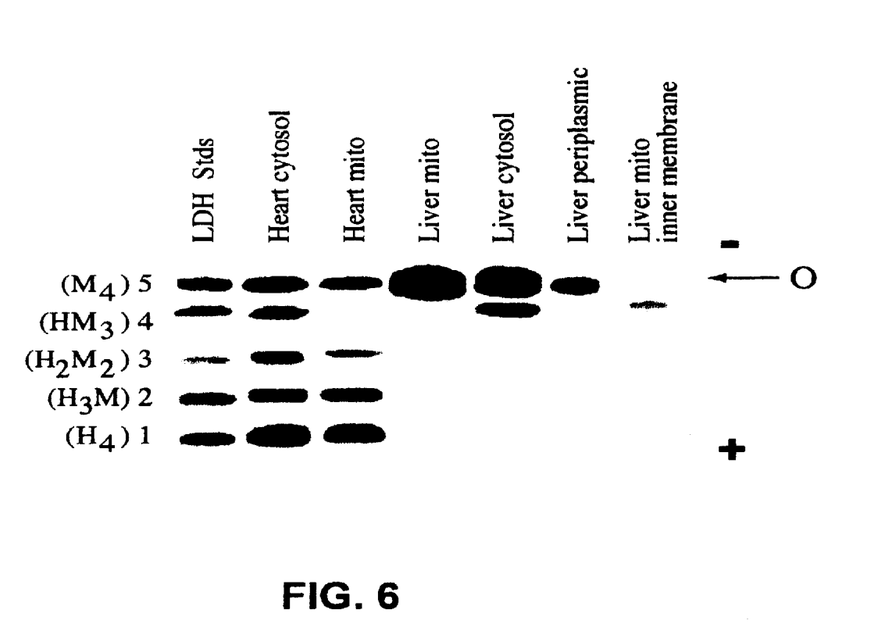

(3): Presence of Lactic Mitochondrial Dehydrogeniase (mLDH): Mitochondria were isolated from rat liver and heart by standard techniques of cell fractionation. Subsequently, mitochondria were treated by gel electrophoresis and the results displayed in FIG. 6. The results indicate presence of mitochondrial LDH, which is mainly of the H4 isoenzyme in heart and red skeletal muscle (not shown). In contrast, liver mitochondria contain only the LDH5 isoform, whereas both LDH4 and LDH5 are present in cytosol of rat liver. These results support the conclusion of separate cytosolic and mitochondrial pools of LDH in rat muscle, liver and heart. Again, the presence of LDH in human muscle mitochondria has been demonstrated (Dubouchaud et al.)

Accordingly, it is desirable to have an alternative physiologically compatible therapeutic compound based on lactate, not pyruvate for lactate is the monocarboxylate selected by nature for exchange in the blood and between and among cells, tissues, organs and intracellular compartments. Again, pyruvate added to the circulation will need to be converted to lactate prior to entry into cells. The sites of this conversion will be erythrocytes or cytosol of cardiac and skeletal muscle cells. Therefore, provision of pyruvate will only slow delivery of monocarboxylate material for mitochondrial oxidation.

(2) Use of Lactate Thiolester as an Energy Source Supplement During Exercise and Recovery Recent advances in basic biochemistry and exercise physiology have shown that the formation and removal of lactic acid is an integral part of both digestive and metabolic processes. Further, as lactate is a fuel for the heart (vide supra), lactate is also a major energy source in working skeletal muscle.

According to the 'Glucose Paradox' hypothesis (reviewed by Foster, 1984, also see Newgard et al., 1983), dietary carbohydrate courses an indirect route before becoming liver glycogen. It is known that dietary carbohydrate is digested and then enters the portal circulation (i.e., that vein between the small intestine and the liver) largely as glucose.

In contrast to traditional theories which hold that the liver extracts large amounts of portal blood glucose for synthesis of glycogen, it is now believed that portal glucose bypasses the liver and enters the systemic circulation through the hepatic vein. Much of this glucose then reaches the resting musculature, where it is either stored as glycogen or converted to lactic acid. This lactic acid then either diffuses or is transported from the sites of production and reaches the systemic circulation. Much of the circulating lactic acid is removed by the liver.

In the glycogen-depleted liver, lactic-acid becomes the preferred precursor material from which to synthesize glycogen. Because glycogen is paradoxically synthesized by a rather circuitous pathway, the process is alternatively termed the Glucose Paradox, or the Indirect Glucose to Liver Glycogen Pathway.

Figure 7:
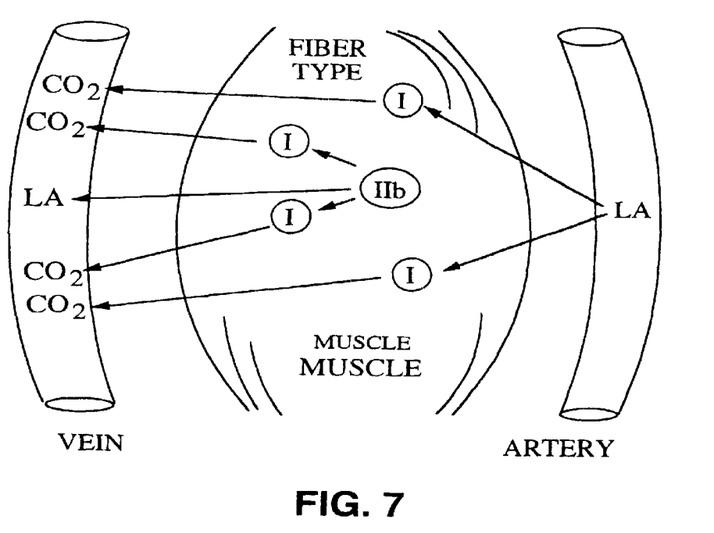
FIG. 7: A diagrammatic representation of the biochemical pathways known as the 'Lactate Shuttle', by which lactate formed in some tissues, such as contracting white skeletal muscle fibers (FG, fast glycolytic, Type IIb), provides an energy source for other tissues such as contracting red skeletal muscle (SO, slow oxidative, Type I) fibers and heart. From Brooks, 1984.
Figure 8:
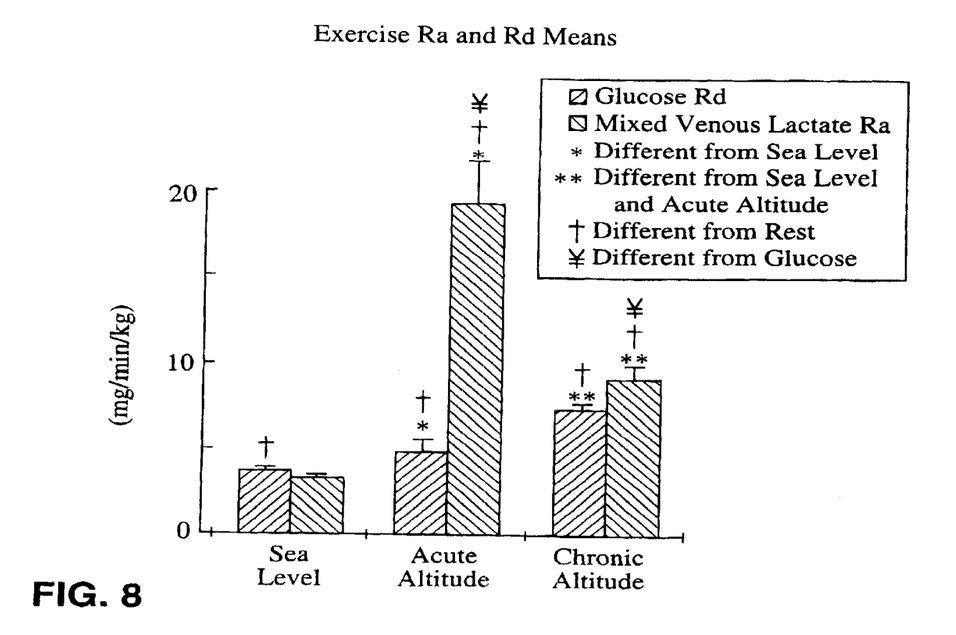
FIG. 8: Effects of altitude exposure and acclimatization on blood glucose disappearance (Rd) and lactate appearance (Ra). Resting values (panel A) are contrasted with those determined during exercise (panel B); (n=6 or 7). Statistical differences as indicated on the figure. From Brooks et al, 1991B.

According to the "Lactate Shuttle" hypothesis (Brooks, 1985, 1986a, 1986b), 1987, 1998, 1999a, 1999b); lactic acid is an important fuel source for exercise as well as resting and exercise-recovery conditions (FIG. 7). During exercise, active fast-twitch muscles produce lactic acid, which is then available as a fuel for slow-twitch, highly oxidative skeletal muscle fibers (Donovan and Brooks, 1983). This process appears to operate all the time as demonstrated in human subjects exercising at sea level (Bergman et al 1999; Mazzeo et al. 1986; Stanley et al. 1985, 1986, 1988), or high altitude (Brooks et al., 1991, 1992). In fact, based on conclusions conducted on rats (Brooks and Donovan, 1983; Donovan and Brooks, 1983) and humans (Bergman et al., 1999;, Brooks, 1992;, Stanley et al., 1988), lactate appears to be a more important fuel for muscular exercise than does glucose, especially during sustained exercise and recovery from sustained, exhausting exercise (FIG. 8).

Results of studies conducted by Gladden and associates (1991, 1994) on canine muscles made to contract in situ support observations made on human subjects. The data clearly show that working canine muscles consume and utilize lactate in a concentration-dependent manner.

Beyond the work of Brooks and associates whose studies have focused on exercising rats and humans, data of Richter et al. (1988) also show that working human skeletal muscle can consume and utilize blood lactate in a concentration-dependent manner. Further, their results show that when a muscle takes up lactate, it decreases its use of glucose.

The oxidation of lactic acid during exercise can be appreciated on both relative and absolute bases. Of the lactic acid produced and removed during exercise, approximately 75% is removed by oxidation and 20 % is converted to glucose (Bergman et al. 1999; Donovan, C. M. and G. A. Brooks, 1983; Stanley et al., 1988, Brooks et al, 1991b, 1992). Of this latter portion, most will ultimately be oxidized also (Brooks, and Donovan, 1983, Brooks et al. 1992). Quantitatively, lactic acid oxidation exceeds glucose oxidation during exercise with 10–25% of the total energy supplied derived from lactic acid oxidation. These findings suggest that it may be desirable to employ lactic acid as a supplement during and/or after exercise.

However, the use of lactic acid as a fuel in the body carries with it potential penalties. Lactic acid accumulation in the muscle is painful and interferes with contraction processes. Further, large amounts of lactic acid in the blood cause pH to fall which is physically and psychologically distressing to the performer. These disadvantages are associated with the hydrogen ion ($H^+$, or proton) which results when lactic acid dissociates in aqueous solutions. For these reasons lactic acid accumulation has long been suspected as a cause of muscle fatigue (Brooks et al., Exercise Physiology: Human Bioenergetics and its Applications, Chapter 33, Mayfield, Mountainview, Third Edition, 2000).

Therefore, it may be advantageous to provide a carbohydrate derived fuel source to an individual engaged in prolonged, strenuous exercise, and it would be more efficacious to provide the carbohydrate energy in the form of a 'lactic acid-like' substance which would provide a more immediate fuel source.

Thus, on the bases of both the "Glucose Paradox" and 'Lactate Shuttle' concepts, providing a 'lactic acid-like' material to athletes during exercise and recovery from exercise would also augment the beneficial effects of providing dietary glucose.

In addition to an energy deficit, sustained exercise also results in dehydration and loss of electrolytes (Brooks et al., 1996). Studies of gastrointestinal absorption have shown that dilute (2–8%) solutions of carbohydrate-electrolyte solutions do not hinder, but may promote gastric and intestinal emptying. Thus, a side benefit of supplying energy in the form of a lactate-containing compound is the ability to provide minor amounts of inorganic lactate salts in solution (e.g., sodium, potassium, magnesium, and calcium). In contrast to sarcolemmal transport which is hydrogen ion ($H^+$)-mediated, intestinal lactate (and glucose) is sodium ($Na^+$)-mediated. Thus, inclusion of 0.2% $Na^+$-lactate with 2% LNACE, and 2-4% other simple sugars and multi-dextrans, would yield a solution that readily promotes fluid, electrolyte, and energy balance and restoration in athletes and other active persons. Similarly, such a beverage would represent an ideal means to treat diarrhea in infants and others.

As already indicated, reactive oxygen species (ROS) can be generated when ischemic tissues are reperfused. Not withstanding the involvement of ROS in reperfusion injury, during sustained, high-intensity exercise when the rate of oxygen consumption is high and sustained, the potential for ROS generation is significant (Davies et al., Viguie et al.). Thus, physical exercise carries with it potential for damage to muscle, heart and blood cells.

Accordingly, it is desirable to produce an energy supplement for exercising individuals based on lactate and the ROS trapping amino acid, N-acetylcysteine. Further, it is desirable to produce an energy-yielding supplement that will facilitate hydration and electrolyte balance in individuals engaged in, or recovering from sustained exercise.

In accordance with the present invention, in addition to providing an antioxidant thiolester for cardiac resuscitation and prevention of reperfusion injury, LNACE is presented as a novel method and composition beneficial to a mammal's fluid, electrolyte and carbohydrate balance during exercise and subsequent recovery are provided.

In one aspect, the invention provides a method of supplying nutritional supplementation to humans and other mammals by means of an aqueous solution of at least one lactic acid salt. This solution is administered in oral dosage form to the host in an amount sufficient to affect the mammal's fluid, electrolyte or carbohydrate balance during exercise and/or subsequent recovery.

In another aspect, a nutritional supplement is provided comprising an aqueous solution of at least one lactic acid salt in an amount sufficient to affect a mammal's fluid, electrolyte or carbohydrate balance during exercise and/or subsequent recovery.

In other aspects, the present nutritional supplement includes mixtures of organic and inorganic lactic acid salts, lactate polymers, and/or simple complex carbohydrates. Such mixtures containing fructose, glucose polymers and larger polysaccharides for provision of fuel energy via enteral (oral) administration rep[resent a different adaptation of the composition than for cardioplegic administration into the blood.

SUMMARY OF THE INVENTION

Accordingly, the global objective of this invention to provide a new and improved lactate compound.

Specific objectives of this invention are:

(1) to provide a new and improved method to provide energy to the stressed heart, (2) to provide a new and improved method to protect cells, tissues, organs and intact individuals from reactive oxygen species (ROS), from reperfusion injury following ischemia, and

(3) to provide a new and improved method to supply supplemental energy to exercising individuals.

To achieve the foregoing objects and in accordance with the purpose of the invention, as embodied and broadly described herein, the novel lactate compound of this invention comprise a lactate thiolester. Preferably, the thiol is cysteine or methionine. In a particularly preferred form, the compound is a N-acetyl ethyl ester of the cysteine or methionine amino acids.

The general form of the compound is:

where R is selected from ethyl, methyl, and alkyl groups. For example the compound could include a ethyl group as shown.

The invention is directed to use of the novel lactate compound for oral consumption or for reperfusion of tissue and organs both in vivo and in storage. Accordingly, the invention includes methods for providing fluid, energy and electrolytes to physically active persons or those exposed to hot, and hot-humid environments, as well as for the preservation of tissue deprived to oxygen through events including, but not limited to, coronary infarction, stroke, mesenteric infarction, organ transplant (during preservation and intravenously after grafting to the organ), including amputated limbs. The compound is also believed well suited to treatment of acetaminophen poisoning to the liver that depletes liver glutathione stores leading to acute hepatic necrosis.

It is believed that lactate provides a ready source for cellular mitochondrial oxidation and that the thiol group from cysteine scavenges ROS as well as provide a precursor for GSH synthesis. Accordingly, the subject novel compound provides a stable, and physiological compound with the beneficial result of delivering lactate and a thiol.

BRIEF DESCRIPTION OF THE DRAWINGS

FIG. 2: L(+) and D(−) lactate transport kinetics in rat sarcolemmal vesicles at various concentrations of isomers. Data are mean±SEM. Lineweaver-Burk plot of the L(+) lactate data. From Roth and Brooks, 1990a.

FIG. 4: Reproduction of a Clark $O_2$ electrode tracing indicating inhibition of mitochondrial oxygen consumption in rat liver mitochondria with lactate or pyruvate as substrates in presence of CINN. Respiration is not affected with succinate as substrate. From Brooks et al., 1999a.

FIG. 6: Agarose gel electrophoresis of LDH in mitochondria from rat liver and heart. LDH isoenzyme patterns differ between cytosol and mitochondria in both tissues. From Brooks et al., 1999a.

DETAILED DESCRIPTION OF THE PREFERRED EMBODIMENTS

As described above, timely coronary reperfusion as treatment for acute myocardial infarction improves cardiac performance, reduces myocardial infarct size and improves survival rates. However, there is concern that reperfusion may cause further injury to the myocardium, called "reperfusion injury."

More particularly, experimental studies have demonstrated that myocardium reperfused after reversible ischemia exhibits prolonged depression or "myocardial stunning".

There is evidence that reperfusion of ischemic myocardium results in the generation of ROS and that a burst of ROS production at the time of reperfusion causes myocardial damage. Accordingly, attempts need be made to provide lactate compounds that facilitate cellular and mitochondrial entry of a fuel energy source as well as trap and/or prevent the formation of ROS.

The present invention is a novel compound including a lactate moiety that provides energy for mitochondrial oxidation, and a thiol moiety that traps ROS. Accordingly, the present compound provides dual functionality in an effective and highly efficient manner and in a physiologically soluble molecule. In addition, the compounds are degraded to physiological and safe metabolites (lactate, cysteine or methionine). Lastly, the present inventive compound is equally applicable to use in the preservation of organs removed for transplantation.

The inventive compounds demonstrate the following characteristics:
(i) water solubility
(ii) no ionic charge to facilitate diffusion through cell membranes, but the compound could also be administered in combination with counter-ions such as $Na^+$, $K^+$, $Mg^{++}$, $Ca^{++}$, or $NH_4+$;
(iii) metabolizable to physiological compounds; and
(iv) stability in solution ex vivo.

The compounds are generally a thiolester of lactate and a sulfur amino acid, for example cysteine and/or methionine. Preferably, any ionizable functions on the amino acids molecules are blocked by easily removable radicals, such as ethyl and N-acetyl groups. The most preferred compound is formed of lactate and N-acetylcysteine ethyl ester.

An embodiment of the invention is a solution of a thiolester of lactate and a sulfur amino acid. In one embodiment the solution comprises an aqueous solution comprising about 1–10% w/v of a mixture consisting of about 10–20% an inorganic salt of lactic acid and about 80–90% LNACE. In this embodiment the inorganic lactic acid salt can be selected from the group consisting of sodium lactate, potassium lactate, magnesium lactate, calcium lactate, and ammonium lactate. The aqueous solution can additionally comprise simple and or more complex carbohydrates. The simple carbohydrates can include glucose or fructose. More complex carbohydrates appropriate for the solution include carbohydrates selected from the group consisting of glucose polymers from five to ten monomeric units.

The invention will now be described with reference to the following examples, intended to describe, but not limit the invention to any particular form of synthesis or manufacture.

Synthesis of LNACE

In a three-neck flask of 500 ml freshly distilled lactic acid (9.06 g., 0.102 mol) and N-hydroxy-succinimide (11.82 g, 0.102 mol) in dry tetrahydrofurane (THF) (180 ml) is stirred under nitrogen and is cooled in a ice bath. Dicyclohexyl-carbodiimide (21.2 g, 0.102 mol) dissolved in dry THF (150 ml) is added slowly to the stirred cooled mixture over approximately 1 hr. Then, the reaction mixture is to be stirred at room temperature for 2.5 hr. followed by slow addition of N-acetyl-L-cysteine ethyl ester (6.81 g., 0.033 mol) dissolved in 20 ml dry THF over approximately 1 hr. The reaction is stirred overnight at room temperature under a nitrogen atmosphere.

After evaporating the THF, the residue should be suspended in ethyl acetate (750 ml) and is kept for 4–6 hr at 0° C. Dicyclohexyl urea (DCU) is then filtered and discarded: the ethyl acetate solution is washed three times with water (3×100 ml). It is then dried over anhydrous sodium sulfate and concentrated under vacuum.

The product (17–18 g) needs to be further purified by using column chromatography. A column of 5 cm diameter is filled with silica gel (180–200 g., 60 Angstrom flash chromatography from Aldrich). The product is dissolved first in a minimum quantity of ethyl acetate:hexane (60:40). Column fractions (e.g., 50 ml aliquots) are collected and monitored by TLC using either iodine or UV light. The fractions containing the product are combined and solvents are removed under reduced pressure. The residue is dissolved in chloroform (300 ml), first washed with 5% HCl (2×30 ml) and then saturated NaCl (3×60 ml). The organic layer is dried over anhydrous sodium sulfate, filtered, and the solvent evaporated. The residue is dissolved in a minimum quantity of chloroform and petroleum ether is added until the solution became turbid. The suspension is kept overnight in the refrigerator and then filtered to get the pure crystallized product. The compound is dried under vacuum over $P_2O_5$ to a yield of approximately 6.5 g.

What is claimed is:

1. A method of facilitating fluid, carbohydrate and electrolyte balance in a mammal, the method comprising the step of orally, intravenously, or intracoronarily administering to the mammal an effective amount of a lactate thiolester having the formula:

wherein R is a proton or an alkyl radical.

2. The method of claim 1, wherein the lactate thiolester is lactate N-acetyl cysteine thiolester.

3. The method of claim 1, wherein the lactate thiolester is lactate N-acetyl methionine thiolester.

4. The method of claim 1, wherein the lactate thiolester is a lactate thiol ethyl ester.

5. The method of claim 1, wherein the lactate thiolester is in a solution comprising about 1–10% w/v of a mixture consisting of an inorganic salt of a lactic acid and about 80–90% LNACE.

6. The method of claim 5, wherein the inorganic salt is selected from the group consisting of sodium lactate, potassium lactate, magnesium lactate, calcium lactate, and ammonium lactate.

7. The method of claim 5, wherein the solution further comprises at least one carbohydrate.

8. The method of claim 7, wherein the carbohydrate is selected from the group consisting of glucose and fructose.

9. The method of claim 7, wherein the carbohydrate is selected from the group consisting of glucose polymers from five to ten monomeric units.

10. A solution for facilitating fluid, carbohydrate and electrolyte balance in a mammal, the solution comprising an inorganic lactic acid salt and LNACE.

11. The solution described in claim 10, wherein the total amount of the inorganic lactic acid salt and the LNACE is from about 1% to about 10% w/v of the solution.

12. The solution described in claim 11, wherein the total amount of the inorganic lactic acid salt and LNACE comprises about 10–20% inorganic lactic acid salt and about 80–90% LNACE.

13. The solution of claim 12 wherein the inorganic lactic acid salt is selected from the group consisting of sodium lactate, potassium lactate, magnesium lactate, calcium lactate, and ammonium lactate.

14. The solution of claim 12 further comprising at least one carbohydrate.

15. The solution of claim 14 wherein the carbohydrate is selected from the group consisting of glucose and fructose.

16. The solution of claim 14, wherein the carbohydrate is selected from the group consisting of glucose polymers of from five to ten monomeric units.

17. The solution of claim 14, wherein the carbohydrate is provided in accordance with the following dosages:

(A) mono- and disaccharide simple carbohydrates in a final concentration of approximately 0.4 to 2.0 weight percent; and (B) polysaccharide complex carbohydrates in a final concentration of approximately 0.8 to 4.0 weight percent.

18. A solution for facilitating fluid, carbohydrate and electrolyte balance in a mammal, the solution comprising about 7% w/v of a mixture consisting of 80% LNACE and 20% sodium lactate.

19. An improved method for preserving tissue deprived of oxygen, the method comprising the step of treating the tissue with an effective amount of a solution containing lactate thiolester having the formula:

wherein R is a proton or an alkyl radical.

20. The method of claim 19, wherein the lactate thiolester is selected from the group consisting of lactate N-acetyl cysteine thiolester and lactate N-acetyl methionine thiolester.

21. The method of claim 19, wherein the solution contains a lactate thiol ethyl ester.

22. The method of claim 19, wherein the tissue comprises an organ removed from a living organism and the step of treating comprises perfusing the organ with the solution.

23. The method of claim 22, wherein the solution contains a physiological electrolyte component.

24. The method of claim 19, wherein the tissue is a cardiac muscle in a human in vivo and the step of treating comprises orally, intravenously or intracoronarily administering to the human an effective amount of the solution enough to increase the cardiac output of the human.

25. The method of claim 24, wherein the lactate thiolester is selected from the group consisting of lactate N-acetyl cysteine thiolester and lactate N-acetyl methionine thiolester.

26. The method of claim 24, wherein the solution contains a lactate thiol ethyl ester.

* * * * *